April 15, 1958 J. R. SALSA Plant Pat. 1,695
PLUM TREE
Filed Sept. 3, 1957
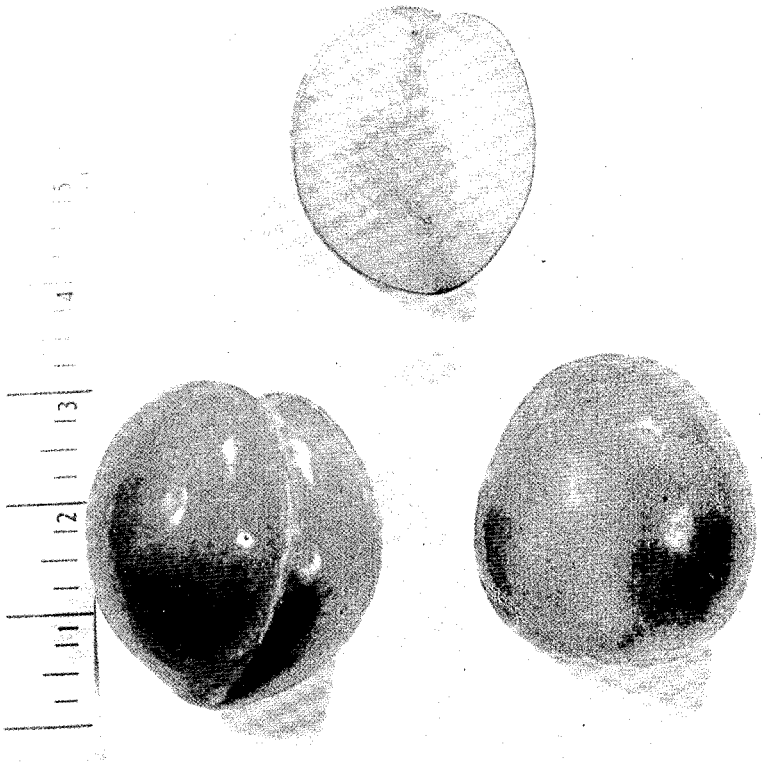
INVENTOR
John R. Salsa
By Orville M. Kile
Plant Patent Agent United States Patent Office Plant Pat. 1,695
Patented Apr. 15, 1958

1,695

PLUM TREE

John R. Salsa, Visalia, Calif.

Application September 3, 1957, Serial No. 681,869

1 Claim. (Cl. 47—62)

My present discovery relates to an improved variety of plum tree, resembling in many respects the well-known California variety, Late Santa Rosa (unpatented), but differing from it in many important respects relating principally to its growng, ripening, coloring, and shipping qualties and to its freedom from "splits" so common in the Late Santa Rosa variety.

My new variety is probably the result of cross-polination between a Late Santa Rosa blossom and an unknown pollen parent, but could be a seedling sport. It occurred in my orchard and nursery rows located on the outskirts of Visalia, California, specifically on Walnut Avenue east of Giddings Avenue. I grow a number of Late Santa Rosa seedlings each year to use as budding stock to replenish my orchards. I bud Late Santa Rosa buds on most of these seedlings. Ordinarily these result in trees and fruit identical with the parent trees, but in this one case, where the seedling was not budded, a distinctly new variety developed. This was not evident until several years had passed, since the tree itself seemed quite similar to the parent Late Santa Rosa trees. This one tree grew in a row with the other trees and under the same conditions of soil, water and climate.

When the first blossoms opened I noted that they opened three of four days ahead of the surrounding trees of the Late Santa Rosa variety. When the first plums matured notable differences became evident to me as will be hereinafter pointed out. In view of the good appearance and other qualities of this plum, and after tending and observing this tree it became apparent to me that it was a new and distinct variety.

I have successfully reproduced this new variety asexually, both by grafts on older trees and by budding. The resulting plums seem identical in every respect with those of the parent tree. This asexual reproduction was done by me on my farm located as set forth above.

The accompanying illustrations show in full color, as nearly as the expert color photographer could reproduce them, two mature typical plums of my new variety together with a sectional view showing the relatively small seed. However, these illustrations do not show the grayish "bloom" that typically covers the ripe fruit while on the tree. Handling soon removes this bloom except in the crease or suture where it is still visible in the photograph. On the tree the ripe red fruit covered with the grayish bloom gives a purplish or bluish color effect. This photograph was made while the plums were still in the "hard-ripe" stage and therefore shows little juice in the cut section although the plum when fully ripe is quite juicy. Also the color of the cut flesh in the photograph is somewhat lighter than when fully ripened.

The tape measure alongside indicates the large size of the fruits although the picture is somewhat foreshortened, since the camera could not be placed directly above the fruits to be photographed.

In the following description the technical color terms used are those of Ridgway's Color Standards and Nomenclature, but ordinary dictionary color terms are also used at points where color is relatively unimportant and no claim to novelty in color is made.

The tree is apparently identical in size, shape and coloring with the Late Santa Rosa trees growing alongside under similar conditions.

Growth: This new variety makes more rapid growth from grafts than does Late Santa Rosa. Such growth during the current season was on July 22 approximately seven feet above the pruning cut on my new variety as compared with approximately five feet on grafts made at the same time on Late Santa Rosa trees.

Leaves: The leaves are apparently the same in size, shape, and color as those of Late Santa Rosa, being elongated with rather wide base and sharp terminal points, lightly serrated; also medium green rather than dark green in color.

Blossoms: The blossoms are white; open 3 to 4 days earlier than the similar blossoms of Late Santa Rosa grown under identical conditions.

Stems: Stems are short and strong.

The fruit:

*Size.*—Large, 2¼ to 2½ inches in axial diameter and a little less in transverse diameter.

*Shape.*—Has a characteristic point at the blossom end although a small proportion of the fruits on a tree may be rounded—the usual shape of the Late Santa Rosa. With the filattened stem end and the pointed blossom end, this plum may be said to have something of an inverted bell shape. The two sides of the fruit are only slightly unequal.

*Cavity.*—Quite narrow but fairly deep.

*Suture.*—Shallow and smooth.

*Skin.*—Smooth, strong, but not tough; has good shipping quality. The light-colored markings or pigments in the skin appear to stand out plainer than on Late Santa Rosa and to consist of short lines rather than the dots or specks usually seen on Late Santa Rosa.

An important feature of this new variety is its relative freedom from splitting of the skin. A principal reason that Santa Rosa is being discarded by many growers is its tendency to split. This usually occurs on 5 percent or more of the fruits and often on 10 to 12 percent—a heavy loss, since no split fruits are shipped. Some seasons my new variety has shown no splits at all and during the current season, when heavy watering was followed by a few days of very hot sun, only a few slight splits occurred.

Fruit set habits: Another important feature of this new variety is the absence of June drop. With Late Santa Rosa and many other varieties the usual heavy June drop makes it necessary when thinning to allow for this late drop of fruit. This causes part of the strength of the tree to be expended on fruits which will later drop off. With no June drop this new variety can be thinned to the desired set and all fruits will mature. This probably accounts for the larger average size as compared to Late Santa Rosa.

Progression of coloring: Coloring on this new variety starts with a reddish spot at the heel of the plum and gradually spreads from this over most of the plum as ripening progresses. As the plum reaches the tree-hard-ripe stage, the red appears as a somewhat bluish or purplish color as seen through the grayish "bloom." By contrast, the Santa Rosa starts to color up by showing a bluish streak down the suture and spreads sideways from this.

Flesh: The flesh is firm and solid when at shipping stage. The axial section shown in the illustration was photographed when "hard-ripe" and shows little juice, but when the plum fully ripens it has an abundance of juice, sweet in flavor—somewhat sweeter than that of Late Santa Rosa. The flesh is of a slightly yellowish color.

Color: The surface color of the tree-hard-ripe fruit ranges from Carmine (Pl. I) in some areas to Ox-Blood Red in others (Pl. I), with irregular Light Greenish Yellow (Pl. V) areas, the latter originating usually at the stem end and extending into the red areas, with speckled and short-lined effects where the red appears to overlay the greenish yellow color. These greenish-yellow areas may be in part due to shading of the ripening fruit by limbs and leaves.

A grayish bloom covers the entire fruit when undisturbed, but is easily rubbed off when fruit is handled.

As the fruit becomes soft-ripe the red colors deepen somewhat, to Ox-Blood Red (Pl. I) over almost the entire surface, and the greenish yellow disappears.

Pit: Pit is notably small and flat. The flesh clings to it.

Ripening, shipping, and keeping qualities: The strong skin and firm flesh combine to make a plum with excellent shipping qualities. It also has superior keeping quality in that it does not shrink as easily as the Late Santa Rosa and many other varieties.

Slow ripening after coloring is another feature of value to the grower. After coloring, these plums will hold on the tree for a long time before becoming too soft to ship. This is true of all the Santa Rosa type plums as grown in the San Joaquin Valley. Picking and shipping may be spread out over a month of time.

However my new variety does color up four to five days earlier than Late Santa Rosa and since every grower tries to get his fruit to market first, the early coloring is a valuable feature.

Having thus disclosed my discovery, I claim:

The plum tree of the Late Santa Rosa type, substantially as herein described and illustrated, characterized particularly by its vigorous growth from grafts; its earlier blooming and coloring of fruits as compared to its parent varieties; the absence of the "June drop" usual with this type of plum, which permits earlier thinning and consequently larger average size of fruits; the virtual absence of splitting of the skins of fruits; the unique progress of coloration of fruits; and the somewhat pointed shape and inverted bell appearance of the fruit as compared to Santa Rosa.

No references cited.